(12) United States Patent
Bayless et al.

(10) Patent No.: US 6,667,171 B2
(45) Date of Patent: Dec. 23, 2003

(54) ENHANCED PRACTICAL PHOTOSYNTHETIC $CO_2$ MITIGATION

(75) Inventors: David J. Bayless, Athens, OH (US); Morgan L. Vis-Chiasson, Athens, OH (US); Gregory G. Kremer, Athens, OH (US)

(73) Assignee: Ohio University, Athens, OH (US)

( * ) Notice: Subject to any disclaimer, the term of this patent is extended or adjusted under 35 U.S.C. 154(b) by 132 days.

(21) Appl. No.: 09/908,369

(22) Filed: Jul. 18, 2001

(65) Prior Publication Data

US 2002/0072109 A1 Jun. 13, 2002

Related U.S. Application Data

(60) Provisional application No. 60/218,871, filed on Jul. 18, 2000.

(51) Int. Cl.[7] .................................................. C12M 1/00
(52) U.S. Cl. ................................ 435/292.1; 435/297.2
(58) Field of Search ............................ 422/168, 186; 435/292.1, 297.1, 297.2, 297.4

(56) References Cited

U.S. PATENT DOCUMENTS

| | | | | |
|---|---|---|---|---|
| 4,253,271 A | * | 3/1981 | Raymond | 47/1.4 |
| 4,446,236 A | * | 5/1984 | Clyde | 435/292.1 |
| 4,676,956 A | * | 6/1987 | Mori | 422/186 |
| 4,999,302 A | * | 3/1991 | Kahler et al. | 435/266 |
| 5,104,803 A | * | 4/1992 | Delente | 435/292.1 |
| 5,554,291 A | * | 9/1996 | Scanzillo et al. | 210/615 |
| 6,083,740 A | * | 7/2000 | Kodo et al. | 435/266 |

FOREIGN PATENT DOCUMENTS

| | | | |
|---|---|---|---|
| DE | 3607864 A | * | 9/1986 |
| JP | 404190782 A | * | 7/1992 |

OTHER PUBLICATIONS

Peschek, G.A. et al; Repsiratory of the Nitrogenase in dinitrogen–fixing cyanobacteria, 1991. Plant Soil 137 (1), pp. 17–24.*

* cited by examiner

*Primary Examiner*—David A. Redding
(74) *Attorney, Agent, or Firm*—Jason H. Foster; Kremblas, Foster, Phillips & Pollick

(57) ABSTRACT

This process is unique in photosynthetic carbon sequestration. An on-site biological sequestration system directly decreases the concentration of carbon-containing compounds in the emissions of fossil generation units. In this process, photosynthetic microbes are attached to a growth surface arranged in a containment chamber that is lit by solar photons. A harvesting system ensures maximum organism growth and rate of $CO_2$ uptake. Soluble carbon and nitrogen concentrations delivered to the cyanobacteria are enhanced, further increasing growth rate and carbon utilization.

15 Claims, 3 Drawing Sheets

ENHANCED PRACTICAL PHOTOSYNTHETIC $CO_2$ MITIGATION

CROSS-REFERENCES TO RELATED APPLICATIONS

This application claims the benefit of U.S. Provisional Application serial No. 60/218,871, filed Jul. 18, 2000.

STATEMENT REGARDING FEDERALLY-SPONSORED RESEARCH AND DEVELOPMENT

The U.S. Government has a paid up license in this invention and the right in limited circumstances to require the patent owner to license others on reasonable terms as provided for by the terms of Program Solicitation Number DE-PS26-99FT40613 awarded by the U.S. Department of Energy.

REFERENCE TO A "MICROFICHE APPENDIX"

(Not Applicable)

BACKGROUND OF THE INVENTION

1. Field of the Invention

This invention generally relates to gas cleaning systems, and more specifically to a biologically-based absorbing apparatus and method to reduce emissions from fossil burning units.

2. Description of the Related Art

The U.S. produces an estimated 1.7 billion tons of $CO_2$ annually from the combustion of fossil fuels. $CO_2$ is a reflector of infrared radiation, so its presence helps "keep" heat in the atmosphere, making the surface temperature warmer than if there was no $CO_2$ in the atmosphere. It is estimated that at present growth rates, $CO_2$ levels in the atmosphere will increase from 350 ppmv (at present) to 750 ppmv in as little as 80 years. In fact, to level $CO_2$ concentrations at 550 ppmv, we will have to reduce net $CO_2$ emissions by over 60% from 1990 levels during the next 100 years.

Even if an expensive option for $CO_2$ removal is discovered, which is by no means a certainty, $CO_2$ "disposal" is problematic. U.S. industries consume only 40 million tons of $CO_2$, produced at a much lower price than possible by removing $CO_2$ from flue gas. Therefore, increased consumption of $CO_2$ appears limited, and options for expanded use appear limited and costly.

Sequestration of $CO_2$ in large bodies of water or in deep mines appears to be the most viable present option. However, sending $CO_2$ into the ocean or an abandoned mine is a limited solution. There is no known exact time scale for storage of $CO_2$; it may be centuries, but it also may only be decades. At best, these are temporary solutions. Further, the transportation issues are considerable, even for the less than 30% of all U.S. fossil-fuel burning power plants that are within 100 miles of an ocean. Existing power plants, with capital values in the hundreds of billions of dollars, are at risk if tens of thousands of miles of specialized pipelines must be installed to transport separated $CO_2$.

The use of ocean-based sinks could present significant problems. It will be necessary to add large amounts of iron to the ocean to use the vast quantities of $CO_2$ stored in the sinks, resulting in uncontrolled growth of certain organisms. Weed plankton, the most likely organisms to grow, will not provide sufficient nutrients for the food webs, and there is a high probability of significant negative environmental impact. In the case of $CO_2$ stored at the bottom of the ocean in lakes, the adverse effects on the ocean-floor ecosystem cannot be predicted, but are likely to be considerable.

Another existing option involves biological carbon sequestration in outdoor ponds. However, there are inherent inefficiencies related to this solution for $CO_2$ sequestration, primarily due to the amount of cyanobacteria that can be grown in a given volume. For example, if 2,000,000 $m^2$ of photosynthetic surface area is required for 25% reduction of $CO_2$ emissions from a power plant, that is equivalent to almost 500 acres of surface. Very few existing plants have 500 acres available to them and fewer could afford to convert 500 acres to a shallow lake or raceway cultivator. Also, there are serious questions about how to distribute the flue gas (or separated $CO_2$) into the lake for maximum growth, not to mention what to do with the gas once it bubbles to the surface. The flue gas would have to be collected again and redirected up a stack to meet other emission requirements. Further, maintaining such a large "lake" during a Midwestern winter would be problematic.

Clearly, other approaches for $CO_2$ control are needed. Research to develop a robust portfolio of carbon management options, including safe and effective photosynthetic carbon recycling, will enable continued use of coal in electrical power generation. Despite the large body of research in this area, virtually no work has been done to create a practical system for greenhouse gas control, one that could be used with both new and existing fossil units.

BRIEF SUMMARY OF THE INVENTION

A method for removing a carbon-containing compound from a flowing gas stream is performed by interposing in the stream a membrane having photosynthetic microbes, such as algae and cyanobacteria, deposited thereon. Applying water and nutrients to the membrane sustains the growth of the microbes, and increasing the volume of water harvests the microbes from the membrane.

The invention also contemplates an apparatus for removing a carbon-containing compound from a flowing gas stream has a membrane interposed in the stream. The membrane has photosynthetic microbes, such as algae and cyanobacteria, deposited thereon.

Figure 1:
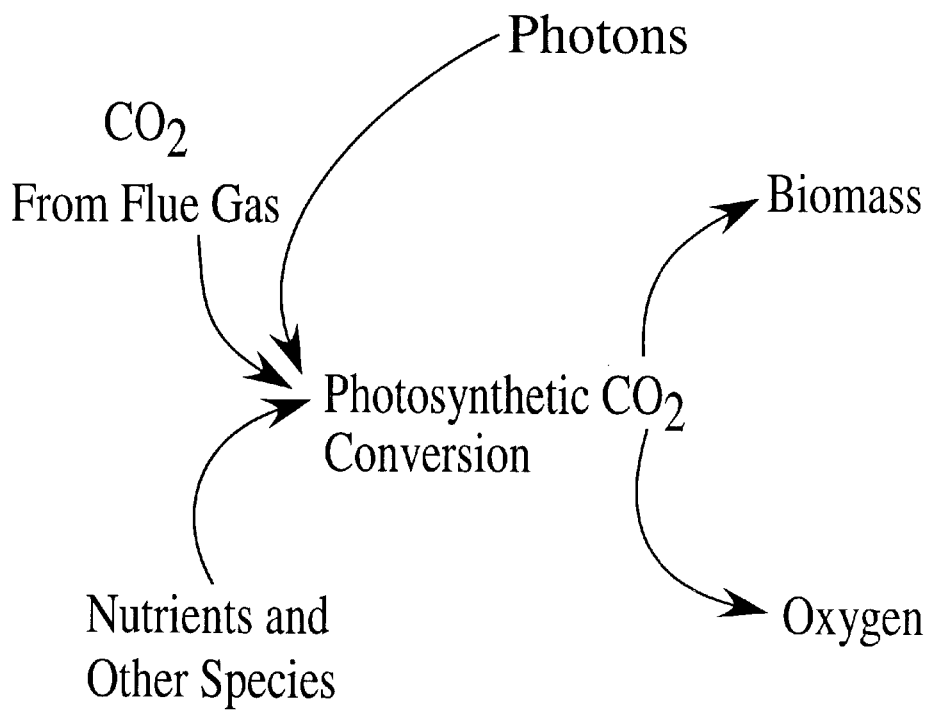
FIG. 1 is a diagram illustrating the carbon sequestration process.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or term similar thereto are often used. They are not limited to direct connection, but include connection through other elements where such connection is recognized as being equivalent by those skilled in the art.

DETAILED DESCRIPTION OF THE INVENTION

Enhanced natural sinks are the most economically competitive and environmentally safe carbon sequestration options for fossil-fuel burning power plants, because they neither require pure $CO_2$, nor incur the costs (and dangers) of separation, capture, and compression of $CO_2$ gas. Among the options for enhanced natural sinks, optimizing the growth of existing photosynthetic organisms in an engineered system is low risk, low cost, and benign to the environment. Additionally, an engineered photosynthesis system has the advantage of being at the source of the emissions to allow measurement and verification of the system effects, rather than being far removed from the emissions source, as is the case with forest-based and ocean-based natural sinks. The invention is suitable for application at existing and future fossil units.

Even though $CO_2$ is a fairly stable molecule, it is also the basis for the formation of complex sugars (food) through photosynthesis in green plants, algae, and cyanobacteria. The relatively high content of $CO_2$ in flue gas (approximately 14% compared to the 350 ppm in ambient air) has been shown to significantly increase growth rates of certain species of cyanobacteria. Therefore, this photosynthetic process is ideal for a contained system engineered to use specially selected strains of cyanobacteria to maximize $CO_2$ conversion to biomass and emitting less of the greenhouse gas to the atmosphere. In this case, the cyanobacteria biomass represents a natural sink for carbon sequestration.

A diagram of the well-understood process of photosynthesis is shown in FIG. 1. Photosynthesis reduces carbon by converting it to biomass. As shown in FIG. 1, if the composition of typical cyanobacteria (normalized with respect to carbon) is $CH_{1.8}N_{0.17}O_{0.56}$, then one mole of $CO_2$ is required for the growth of one mole of cyanobacteria. Based on the relative molar weights, the carbon from 1 kg of $CO_2$ could produce increased cyanobacteria mass of 25/44 kg, with 32/44 kg of $O_2$ released in the process, assuming $O_2$ is released in a one-to-one molar ratio with $CO_2$. A conservative estimate indicates that a 2,000,000 $m^2$ facility powered by collected solar energy could process 25% of the effluent $CO_2$ from a 200 MW coal-fired power plant, producing over 140,000 tons of dry biomass per year. Dried biomass could be used in the production of fertilizer, fermented or gasified to produce alcohols and light hydrocarbons, or directly as a fuel to meet biomass mandates in pending deregulation legislation. Therefore, a photosynthetic system provides critical oxygen renewal along with the recycling of carbon into potentially beneficial biomass.

Optimization of this process in the present invention is based on design of a mechanical system to best utilize photosynthetic microbes. Photosynthetic microbes are microorganisms, such as algae and cyanobacteria, which harness photons to fix carbon-containing gas into carbon-based biomass. Cyanobacteria have been chosen as photosynthetic agents, because they are one of only two groups of organisms capable of growing at the fossil-fired environmental temperatures of 50–75° C. For example, Cyanidium calderium has been shown to be able to fix $CO_2$ under the conditions of the flue gas remediation apparatus at 70–75° C. and below. Cyanobacteria are small in size and grow attached to sediment particles in thermal streams. This is an essential property for growth in a fixed cell bioreactor. Another advantage to using cyanobacteria is amenability to manipulation in the laboratory and thus to a power plant setting. Cyanobacteria in general are mechanically robust making them ideal organisms for use in bioreactors.

Figure 2:
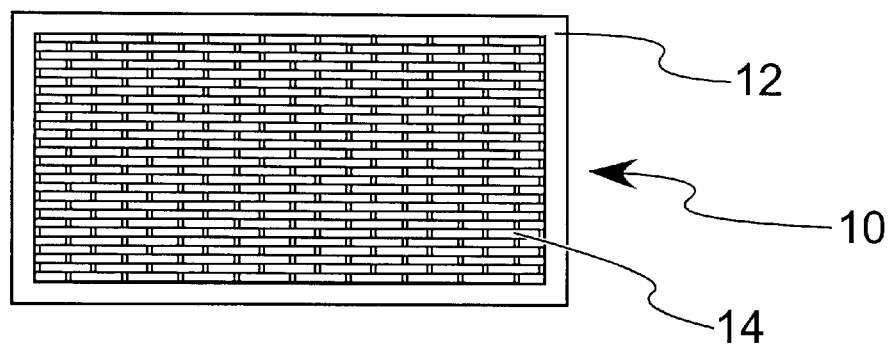
FIG. 2 is a front view illustrating a membrane.

Referring to FIG. 2, the photosynthetic microbes populate a growth surface 10, which is composed of a membrane 14 fastened within a frame 12. The information contained in U.S. Patent Application Serial. No. 60/258,168 to Pasic, et al., is incorporated herein by reference. The growth surface 10 shown in FIG. 2 is rectangular, and the membrane 14 is twenty-one inches long by ten and one-half inches wide, mounted in a frame one half inch thick. However, the size of the membrane 14 may vary depending on the requirements of the power plant in which the inventive apparatus is applied.

Figure 3:
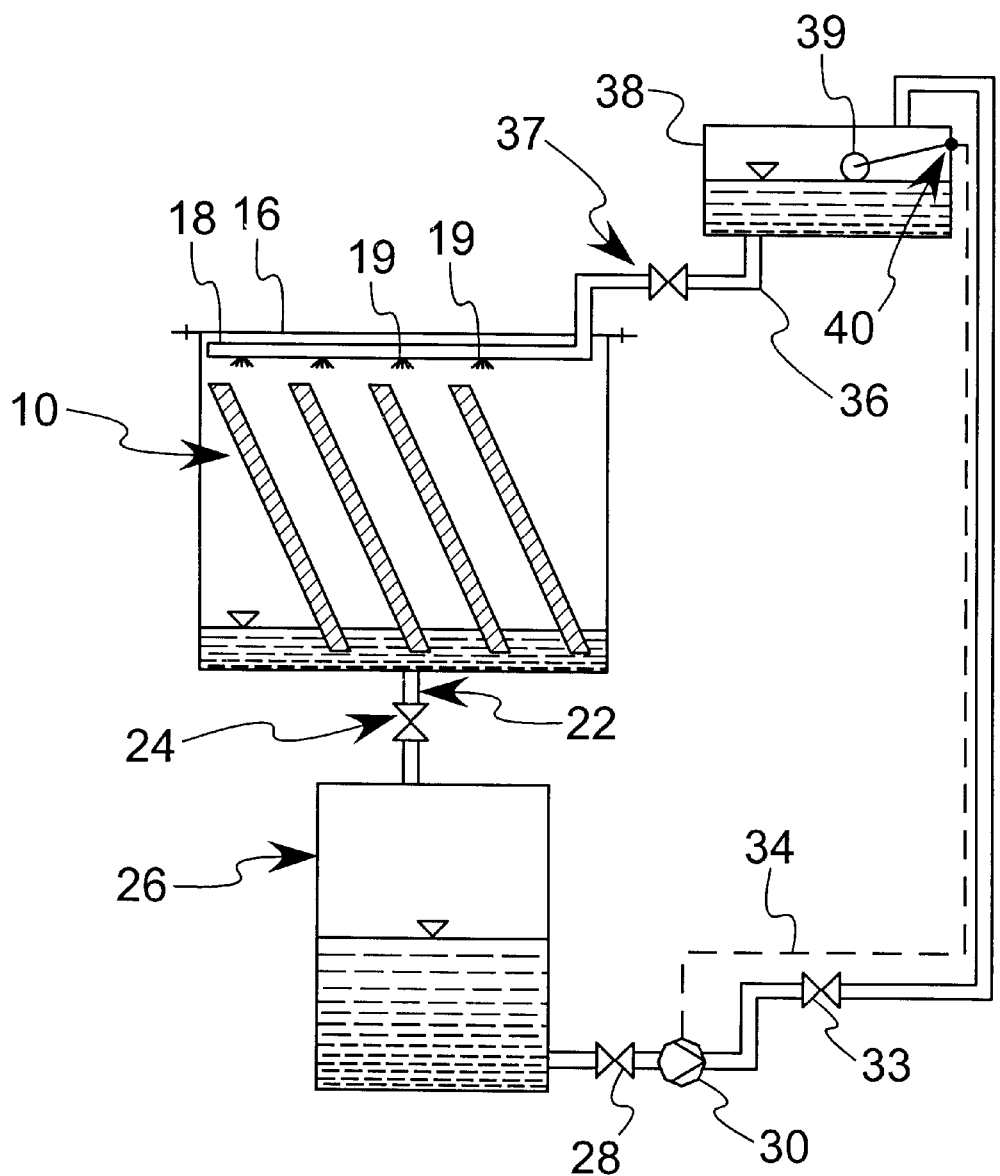
FIG. 3 is a diagram illustrating a solution supply and recirculation system.

The material selection for the membrane 14 is dictated by the mechanical properties necessary for the optimal design in a containment chamber 16 shown in FIG. 3. The membrane 14 should be an inorganic material, such as plastic, to avoid problems with fungi growth. The membrane 14 must be composed of a material that suits the specific microbe used, being non-toxic to the microbe and supporting adhesion. It is essential that microbes supplied to the growth surface 10 be able to grow in the attached state. The growth surface 10 needs to provide reliable structural integrity when exposed to the flue gas environment.

The cyanobacteria are distributed evenly over the membrane 14 to maximize the photosynthetic surface area. Directly pouring a microbial solution over the membrane 14, applying the solution using a pump or an organism-entrained water flow through the membrane accomplishes even distribution.

Figure 4:
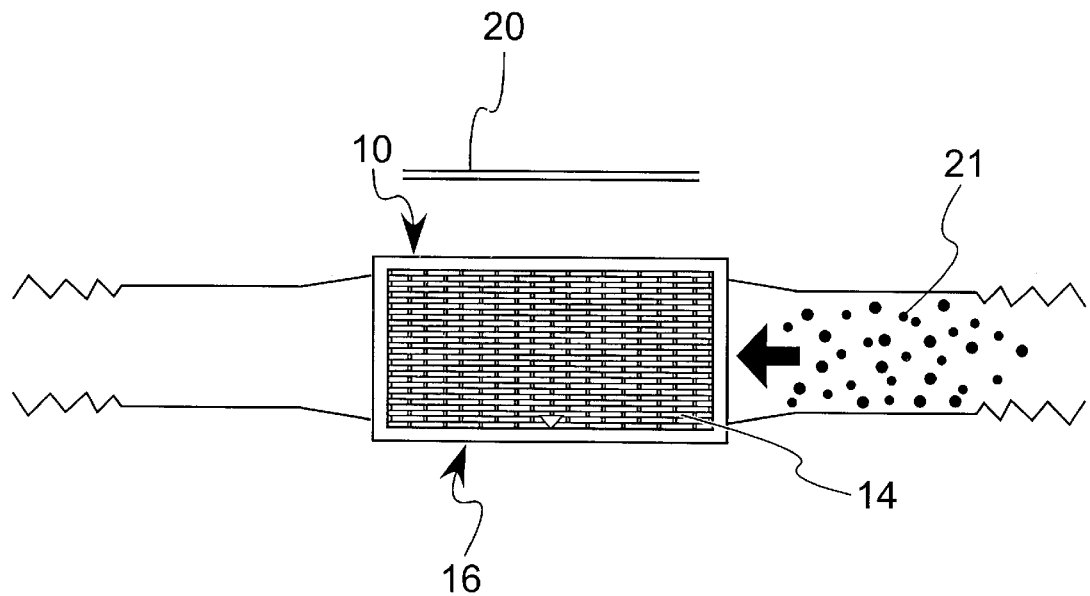
FIG. 4 is a diagram illustrating a flue gas flowing over membrane.

The growth surface 10 is introduced to a carbon-containing gas 21 when placed in the containment chamber 16, which is in the flow path of the gas 21 as shown in FIG. 4. A light source 20 for the microbes uses fiber optics to supply photons for driving photosynthesis. The light source 20 may be positioned above the chamber 16 as in FIG. 4, or in a position relative to the membrane 14 to optimize cyanobacterial growth and carbon dioxide uptake.

In FIG. 4, each growth surface 10 is oriented in the containment chamber 16. The growth surface 10 can be oriented at an angle of ninety degrees relative to the chamber 16, but the angle may vary depending on the needs of a specific unit. The growth surfaces 10 may be fixed in place within the chamber 16, movable in increments, or continuously movable to optimize exposure to the flue gas. The orientation of the growth surface 10 provides minimum power loss due to flow obstruction when in the containment chamber 16.

Experiments were performed at Ohio University using an experimental system called a Carbon Recycling Facility (CRF), which simulates a flue gas environment by having the membrane 14 populated with microbes and contained as shown in FIG. 4. Experiments include weight and visual analysis of the algae grown and harvested.

Harvesting is the removal of mature photosynthetic microbes from the membrane 14 of the growth surface 10. Harvesting is advantageous, because the rate of carbon dioxide consumption decreases as the growth rate of cyanobacteria slows. Therefore, harvesting cyanobacteria to make space for further growth maximizes carbon dioxide uptake. The harvesting method involves flushing the membrane 14 at periodic intervals with a large volume of liquid. The momentum from the large volume of flushing liquid is sufficient to overcome adhesive forces that hold the microbes on the membrane, so many of the microbes are displaced from the membrane 14.

Harvesting occurs in the containment chamber 16 by a differential pressure water supply system, which functions as a nutrient delivery drip system at low delivery pressures and algal harvesting system at high delivery pressures. Under normal conditions the membrane 14 is hydrated by capillary action. Under harvesting conditions, the fluid delivery action is increased, creating a high flow sheeting action that displaces a substantial percentage of the microbes from the membrane 14.

Figure 5:
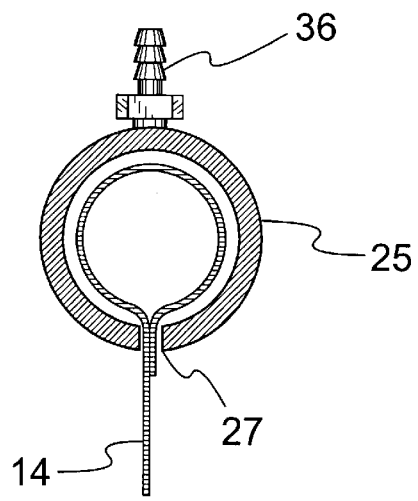
FIG. 5 is a side view in section illustrating the membrane arrangement in the hydrating solution delivery system.

FIG. 5 shows the preferred arrangement for the manifold water delivery system within the containment chamber 16. A pipe 25 receives the growth solution from the supply line 36. The solution flows to the membrane 14 through an opening 27 in the pipe 25. As shown in FIG. 5, in the preferred embodiment an edge of the membrane 14 is held in contact with the inside of the pipe 25, and the rest of the membrane 14 is draped through the opening 27. Because the membrane has capillary passages through which the solution can flow, the solution never has to be sprayed if spraying is desired to be avoided. Instead, capillary flow can supply solution to the algae through the membrane.

Harvesting that results in partial cleaning of the membrane 14 is preferred. Partial cleaning means that after cleaning, enough cyanobacteria remain adhered to repopulate the membrane 14. This is desirable to avoid a growth lag, thereby maximizing carbon dioxide uptake in the system. The harvested cells accumulate in a slurry at the bottom of the containment chamber 16. The harvested cells are removed, and fresh growth solution is applied to the young cells that remain on the membrane 14.

In an alternative embodiment shown in FIG. 3, harvesting is accomplished by administering water and the growth medium by a nozzle 19, either separately or by the same nozzle 19. Harvesting by this method is accomplished through a stream of pressurized water that flows out the nozzle 19 and onto the membrane 14. The force of the impact dislodges the cyanobacteria from the membrane 14. Sufficient cleaning occurs when the water stream is set at a shallow incidence angle and a relatively low velocity, for example between 30 and 40 degrees relative to the growth surface 10. A 90-degree low-flow, full cone whirl nozzle provides a good balance between covering a large area with the water jet, and a gentle partial cleaning. A flat-fan nozzle is also effective when swept or rotated across the coverage area.

Alternatively, or in addition, a solution may be used to chemically promote removal of the microbes from the membrane 14. Most microorganisms have a cation requirement for adhesion, usually calcium (Cooksey and Wigglesworth-Cooksey, 1995). Thus, they can be removed from a surface with calcium ion-complexing agents such as EDTA or EGTA (Cooksey and Cooksey, 1986).

The partially cleaned membrane 14 can be repopulated with actively growing cells removed while cleaning the membrane 14. After cleaning, the slurry of cells and growth solution is agitated to disperse any clumps of algae into individual cells. Then, selective filtration of the slurry separates the large microbial cells that are old or dead from the small cells that are young and alive, and the young actively growing cells are reapplied to the growth surface 10 to repopulate the membrane 14.

In the alternative embodiment shown in FIG. 3, the microbes washed from the membrane 14 may be removed, and the growth solution may be recirculated to the membrane 14 after harvesting. A recirculation system can continuously administer the growth solution to the microbes, while they are subjected to the high temperature gas flowing through the containment chamber 16. As shown in FIG. 3, a growth solution dripping manifold 18 is located at the top of the containment chamber 16. The manifold 18 continuously delivers the growth solution to the algae through a solution supply line 36, through which a solution supply-isolating valve 37 regulates the flow of solution. The growth solution accumulates at the bottom of the containment chamber 16.

The growth solution flows from the containment chamber 16 through a drain line 22. A drain-isolating valve 24 regulates the flow, and the solution is drained into a lower holding tank 26. A pump isolation valve 28 opens a solution recirculation pump 30 and draws the growth solution from the lower holding tank 26, through an inline filter 33, and upwardly to the upper holding tank 38.

The growth solution is pumped into the upper holding tank 38, where a float 39 and a level switch 40 regulate the level of growth solution inside. An electric signal line 34 leads from the level switch 40 to the solution recirculation pump 30, which is activated when the solution reaches a predetermined level in the upper holding tank 38. The level of solution in the upper holding tank 38 is maintained constant by the level switch 40 and the recirculation pump 30.

An alternative or additional step in the process may include nutrient enhancement and delivery. Cyanobacteria mostly easily fix carbon and nitrogen in aqueous form. One possible way to increase carbon and nitrogen content is to use technology known as translating slug flow. Using translating slug flow technology increases concentrations of nutrients, lowers flue gas temperatures, and increases humidity. Slugs create zones of greatly enhanced gas-liquid mass transfer, putting $CO_2$ and NOx into the water as soluble species for the cyanobacteria. Optimal levels of these nutrients maximize cyanobacterial growth.

The cyanobacteria react positively to the conditions established by a translating slug flow reactor immediately upstream of the bioreactor. Translating slugs, which have leading edges of greatly enhanced mass transfer, increase the content of soluble carbon and nitrogen in the liquid used to grow the cyanobacteria. Slugs result when the gas to liquid flow reaches unstable conditions in nearly horizontal pipes. In fact, a slight vertical inline can substantially increase slug frequency and thus increase the rate at which $CO_2$ is transferred to the water.

The process of inducing slug flow (gas-liquid mass transfer) results in vastly enhanced $CO_2$ absorption in the water used to grow the cyanobacteria, and it produces several other advantages. By absorbing $CO_2$ in the water in the slug flow reactor, the flue gas might never need to come directly in contact with the bioreactor. If the $CO_2$ is already in solution, then some cyanobacteria do not require gaseous $CO_2$ for photosynthesis. This offers the advantage of using less thermo tolerant cyanobacteria, because the water temperature from the slug flow reactor is between 35–40° C. If a dual $CO_2$ delivery method is used (some in the aqueous phase, some in the gaseous phase), the interaction of large volumes of cooled water with the flue gas, and the subsequent saturation of the growth surfaces with the enhanced level of soluble carbon and nitrogen increases growth rate of the photosynthetic organism.

The use of mature cyanobacteria is an advantage to using this process. Mature cyanobacteria can produce value-added products and energy. One advantageous use for the post-processed cyanobacteria is in the combustion of cyanobacteria and coal as a blended fuel in fluidized bed combustion to power Stirling cycle free piston engines. With pending electric deregulation legislation requiring as much as 7.5% utilization rate of biomass, a viable biofuel and method for utilizing that fuel needs to be found. Dried cyanobacteria have been shown to have a suitable higher heating value, high volatile content, and have suitable ignition characteristics to be co-fired with coal in pulverized coal-fired generation units.

Another benefit is oxygen production. Oxygen is a natural product of photosynthesis. If it is assumed that 1 mole of $O_2$ is formed for each mole of $CO_2$ consumed during photosynthesis, then for every kg of $CO_2$ consumed, (32/44) or 0.73 kg of $O_2$ are produced. This is a significant benefit.

Another benefit is the potential for reduction of other pollutants, sulfur and nitrogen species. In fact, work by Yoshihara et al. (1996) shows considerable nitrogen fixation from NOx species bubbled through a bioreactor, one with poorer mass transfer characteristics than would be found in the process described here.

While this process claims carbon sequestration as its goal, carbon is actually being recycled in this process. Carbon recycling is fundamentally different than sequestration, with several advantages. In sequestration, the carbon is no longer available for use. While $CO_2$ use for enhanced oil recovery has a benefit, $CO_2$ or carbon has little use in other forms of sequestration. With photosynthetic carbon recycling, useful carbon-containing biomass and oxygen are produced from the carbon dioxide. As described, biomass has a number of beneficial uses, including as a fuel to offset the use of fossil fuels, as a soil stabilizer, fertilizer, or in the generation of biofuels (such as ethanol or biodiesel) for transportation use. In addition, the light collection and transmission system designed for the preferred embodiment provides additional electrical power (using the previous example parameters) by converting a portion of the filtered infrared spectrum using photovoltaics.

A first experiment was performed at 120° F. under controlled parameters of $CO_2$ concentration. Experiment I was illuminated at 18.25 $\mu mol\text{-}s^{-1}m^{-2}$ measured at the base of the experimental containment after the algae samples were loaded over the screens in the containment. Again the amount of algae sample loaded over each screen was 3000 ml giving total loading of 12000 ml in the reactor. Table 1.1 gives the weight analysis of 25 ml samples drawn through paper filters for calculation of the weight of algae used for testing.

TABLE 1.1

Dry weight analyses for test samples for Experiment I.

| Filter Number | Volume | Weight before filtering sample | Weight after filtering sample | Difference |
|---|---|---|---|---|
| #1 | 25 ml | 1.7282 gm | 1.7435 gm | 0.0153 gm |
| #2 | 25 ml | 1.6294 gm | 1.6455 gm | 0.0161 gm |
| #3 | 25 ml | 1.8189 gm | 1.8368 gm | 0.0179 gm |
| #4 | 25 ml | 1.7889 gm | 1.8066 gm | 0.0177 gm |
| #5 | 25 ml | 1.7488 gm | 1.7663 gm | 0.0175 gm |
| Total = | 125 ml | | | 0.0845 gm |

The effective amount of algae loaded was 8.112 gm. The simulated flue gas at 120° F. contained 10.0% $O_2$, 5.7% $CO_2$, 700 ppm CO, 1.87 slpm natural gas and 23.92 slpm air.

The light intensity passing through the containment was measured (at the bottom of the reactor), as shown in Table 1.2.

TABLE 1.2

Light intensity passing through the containment for Experiment I.

| Time | Light intensity | |
|---|---|---|
| (hours) | mV | umol-s$^{-1}$m$^{-2}$ |
| 0 | 48.7 | 18.25 |
| 21 | 51.2 | 19.19 |
| 45 | 57.6 | 21.58 |
| 58 | 67.8 | 25.41 |
| 70 | 79.2 | 29.68 |
| 77 | 83.8 | 31.41 |
| 83 | 88.1 | 33.02 |
| 93 | 89.8 | 33.65 |
| 97 | 91.6 | 34.33 |
| 109 | 92.6 | 34.70 |
| 118 | 93.6 | 35.08 |
| 120 | 94.2 | 35.30 |

The Difference in dry weight of four numbers of screens and inline filter was calculated and effective weight was compared with the weight of algae samples loaded. Table 1.3 tabulates the measured dry and differential weights.

TABLE 1.3

Weight analysis of screens and filter for Experiment I.

| | Before trial | After trial | Difference |
|---|---|---|---|
| Screen #1 | 149.1 gm | 150.5 gm | 1.4 gm |
| Screen #2 | 155.6 gm | 157.3 gm | 1.7 gm |
| Screen #3 | 149.7 gm | 151.3 gm | 1.6 gm |
| Screen #4 | 151.7 gm | 151.4 gm | −0.3 gm |
| Filter | 189.1 gm | 193.6 gm | 4.5 gm |
| | | Total = | 8.9 gm |

It was observed during the experiment that Nostoc 86-3 did not change color and remained green, but with reduced density on the screens. In addition, the amount of light intensity passing through the containment showed a continuous rise with time. The observation also supports the decrease in micro algae density as more light passed over the screens. However, the amount of cyanobacteria obtained after trial was more than that initially loaded, indicating a positive growth.

Experiment II was conducted at 120° F. under an illumination of 22.11 $\mu mol\text{-}s^{-1}m^{-2}$ measured at the base of the experimental containment chamber after the algae samples were loaded. Again the amount of algae samples loaded over each screen was 3000 ml giving total loading of 12000 ml in the reactor. Table 2.1 displays the weight analysis of 25 ml samples drawn through paper filters for calculation of the weight of algae for testing.

TABLE 2.1

Dry weight analysis for test samples for Experiment II.

| Filter Number | Volume | Weight before filtering sample | Weight after filtering sample | Difference |
|---|---|---|---|---|
| #1 | 25 ml | 1.7666 gm | 1.7921 gm | 0.0255 gm |
| #2 | 25 ml | 1.7011 gm | 1.7266 gm | 0.0255 gm |
| #3 | 25 ml | 1.7402 gm | 1.7668 gm | 0.0266 gm |
| #4 | 25 ml | 1.8402 gm | 1.8677 gm | 0.0275 gm |
| #5 | 25 ml | 1.6527 gm | 1.6778 gm | 0.0251 gm |
| Total = | 125 ml | | | 0.1302 gm |

The effective amount of algae loaded was 12.500 gm. The simulated flue gas at 120° F. contained 9.5% $O_2$, 6.0% $CO_2$, 500 ppm CO, 1.73 slpm natural gas and 21.33 slpm air.

For this experiment, the illumination was maintained under ON-OFF mode (12 hour cycle) to support the light and dark reactions of cyanobacterial photosynthesis. The light intensity passing through the containment was measured after every 12 hours (at the bottom of the reactor), as shown in Table 2.2.

TABLE 2.2

Light intensity passing through the containment for Experiment II.

| Time (hours) | Light intensity mV | Light intensity $\mu mol\text{-}s^{-1}m^{-2}$ |
| --- | --- | --- |
| 0 | 48.7 | 18.25 |
| 12 | 74.6 | 27.96 |
| 24 | 73.4 | 27.51 |
| 36 | 76.4 | 28.64 |
| 48 | 77*7 | 29.12 |
| 60 | 77.5 | 29.05 |
| 72 | 74.0 | 27.74 |
| 84 | 80.4 | 30.14 |
| 96 | 84.5 | 31.67 |
| 108 | 88.6 | 33.21 |

After 120 hours the growth screens and filter were removed and dried. Table 2.3 tabulates the measured dry and differential weights.

TABLE 2.3

Weight analysis of screens and filter for Experiment II.

| | Before trial | After trial | Difference |
| --- | --- | --- | --- |
| Screen #1 | 146.8 gm | 151.1 gm | 5.3 gm |
| Screen #2 | 148.1 gm | 151.5 gm | 3.4 gm |
| Screen #3 | 150.1 gm | 152.8 gm | 2.7 gm |
| Screen #4 | 148.3 gm | 151.1 gm | 2.8 gm |
| Filter | 137.6 gm | 145.9 gm | 8.3 gm |
| | | Total = | 22.5 gm |

The light intensity passing through the containment showed a continuous but gradual rise in jumps at various intervals. It was also observed that the Nostoc 86-3 changed color to light brown. Cellular study testified that the species were of consistent size with the batch culture of algae and maintained the filamentous morphology of Nostoc. The species were found to be maintaining healthy coloration and were not dying. These results indicate that species Nostoc 86-3 can tolerate 120° F. as observed from the color of the samples after the experiment.

While certain preferred embodiments of the present invention have been disclosed in detail, it is to be understood that various modifications may be adopted without departing from the spirit of the invention or scope of the following claims.

What is claimed is:

1. An apparatus for removing a carbon-containing compound from a flowing gas stream, said apparatus comprising:
    (a) at least one substantially immobile membrane mounted in said gas stream;
    (b) a plurality of photosynthetic microbes, selected from the group of algae and cyanobacteria, on said membrane;
    (c) a water and nutrient delivery device including a liquid-conveying conduit having at least one opening near a top edge of said at least one membrane for delivering water and nutrients in the conduit near the top edge of the membrane, wherein the membrane permits water and nutrients to flow through the membrane by capillary action; and
    (d) means for changing a pressure of the water front a microbe-sustaining pressure, wherein water and nutrients are supplied to the microbes without substantial removal of microbes from the membrane, to a microbe-removing pressure, wherein at least water is applied to the membrane to remove at least some of the microbes from the membrane.

2. An apparatus in accordance with claim 1, further comprising means for cooling the gas upstream of the membrane.

3. An apparatus in accordance with claim 2, wherein the temperature of the gas near said membrane is less than about 75 degrees Centigrade.

4. An apparatus in accordance with claim 1, wherein the temperature of said gas near the membrane is less than about 75 degrees Centigrade.

5. An apparatus in accordance with claim 1, wherein the temperature of said gas is greater than about 50 degrees Centigrade.

6. An apparatus in accordance with claim 1, wherein the water and nutrient delivery device comprises at least one liquid-conveying conduit having at least one opening adjacent the membrane near the top edge of the membrane for injecting the liquid into the membrane.

7. The apparatus in accordance with claim 6, wherein the means for changing a pressure further comprises means for varying the pressure over time between the microbe-sustaining pressure and the microbe-removing pressure.

8. An apparatus in accordance with claim 1, further comprising means for illuminating said photosynthetic microbe with a light source for a period of time.

9. An apparatus in accordance with claim 6, wherein said light source includes fiber optics.

10. The apparatus in accordance with claim 1, wherein said cyanobacteria is Cyanidium.

11. The apparatus in accordance with claim 1, wherein said cyanobacteria is Nostoc.

12. The apparatus in accordance with claim 1, wherein said membrane is a polyester.

13. The apparatus in accordance with claim 1, wherein said membrane is tetraflouroethylene.

14. An apparatus for removing carbon dioxide from a flowing gas stream, said apparatus comprising:
    (a) at least one substantially immobile membrane mounted in said gas stream;
    (b) a plurality of photosynthetic microbes selected from the group of algae and cyanobacteria on said membrane;
    (c) means for illuminating said photosynthetic microbe for a period of time;
    (d) a water and nutrient delivery device including at least one liquid-conveying conduit seating against the membrane near a top edge and openings in the conduit for injecting water and nutrients in the conduit into the top edge of the membrane, wherein the water and nutrients flow at least through the membrane by capillary action; and
    (e) means for changing a pressure of the water from a microbe-sustaining pressure, wherein water and nutrients are supplied to the microbes without substantial removal of microbes from the membrane, to a microbe-removing pressure, wherein at least water is applied to the membrane to remove at least some of the microbes from the membrane.

15. The apparatus in accordance with claim 1, wherein the water and nutrient delivery device further comprises at least one nozzle spaced from the membrane near the top edge of the membrane for spraying the water and nutrients onto the membrane across a gap between the nozzle and the membrane.

* * * * *